United States Patent
Vernon

(10) Patent No.: US 7,045,802 B2
(45) Date of Patent: May 16, 2006

(54) METHOD AND APPARATUS FOR COINCIDENCE IMAGING DIGITAL TRIGGERING

(75) Inventor: Philip Vernon, Aurora, OH (US)

(73) Assignee: General Electric Company, Schenectady, NY (US)

( * ) Notice: Subject to any disclaimer, the term of this patent is extended or adjusted under 35 U.S.C. 154(b) by 384 days.

(21) Appl. No.: 10/723,494

(22) Filed: Nov. 26, 2003

(65) Prior Publication Data

US 2005/0109958 A1    May 26, 2005

(51) Int. Cl.
*G01T 1/172* (2006.01)
(52) U.S. Cl. ............ 250/526; 250/363.03; 250/363.04; 250/363.02; 250/363.09; 250/252.1
(58) Field of Classification Search ................ 250/526, 250/363.03, 363.04, 363.02, 363.09, 252.1
See application file for complete search history.

(56) References Cited

U.S. PATENT DOCUMENTS

| | | | |
|---|---|---|---|
| 4,411,002 A * | 10/1983 | Auger | 375/249 |
| 4,634,896 A * | 1/1987 | Shrinkle | 327/76 |
| 4,837,437 A * | 6/1989 | Forster et al. | 250/336.1 |
| 5,241,181 A | 8/1993 | Mertens et al. | |
| 5,272,343 A | 12/1993 | Stearns | |
| 5,585,637 A * | 12/1996 | Bertelsen et al. | 250/363.03 |
| 6,252,232 B1 | 6/2001 | McDaniel et al. | |
| 6,255,655 B1 * | 7/2001 | Mc Croskey et al. | 250/363.03 |
| 6,362,478 B1 | 3/2002 | McDaniel et al. | |

FOREIGN PATENT DOCUMENTS

EP    747730 A2 *  12/1996

OTHER PUBLICATIONS

Bronstein et al., "High Energy Photon Detection in Positron Emission Tomography" Feb. 14, 2002, Israel Institute of Technology, pp. 1-64.*

* cited by examiner

*Primary Examiner*—Otilia Gabor
*Assistant Examiner*—Christine Sung
(74) *Attorney, Agent, or Firm*—Carl B. Horton, Esq.; Armstrong Teasdale LLP

(57) ABSTRACT

A method for operating a coincidence imaging system is provided. The method includes receiving samples from a detector output and determining an intersection of a first line corresponding to a baseline portion of the detector output samples and a second line corresponding to a pulse rise portion of the detector output samples.

15 Claims, 3 Drawing Sheets

METHOD AND APPARATUS FOR COINCIDENCE IMAGING DIGITAL TRIGGERING

BACKGROUND OF THE INVENTION

This invention relates generally to nuclear medicine imaging systems and, more particularly, to methods and apparatus for providing coincidence imaging in such systems.

Positrons are positively charged electrons that are emitted by radionuclides that have been prepared using a cyclotron or other device. These positions are employed as radioactive tracers called "radiopharmaceuticals" by incorporating them into substances, such as glucose or carbon dioxide. The radiopharmaceuticals are injected into a patient and become involved in such processes as blood flow, glucose metabolism, and protein synthesis.

Positrons are emitted as the radionuclides decay. The positrons normally travel a very short distance before they encounter an electron, and when this occurs, the positron and electron are annihilated and converted into a pair of photons, or gamma rays. This annihilation "event" is typically characterized by two features that are pertinent to positron emission tomography (PET) scanners, namely, each gamma ray has an energy of 511 keV and the pair of gamma rays are directed in substantially opposite directions. An image is created by determining the number of such annihilation events at each location within the field of view.

A PET scanner may include two or more solid-state or scintillation detectors to detect individual photons. Some known scanners include a plurality of detectors that define a ring around a volume of interest. Timing the detection of these events is used to identify the pairs of photons from a single annihilation. To facilitate effective operation, detection events should be able to be timed to ten nanoseconds or less. Each scintillation detector includes a scintillator that converts the energy of each 511 keV photon into a flash of light that is sensed by a photomultiplier tube (PMT). Coincidence detection circuits are coupled to the detectors and record only those photons that are detected simultaneously by two detectors located on opposite sides of some part of the patient. The number of such simultaneous events indicates the number of positron annihilations that occurred along a line joining the two opposing detectors. Within a few minutes hundreds of millions of events may be recorded to indicate the number of annihilations along lines joining pairs of detectors in the ring. These numbers of events are employed to reconstruct an image using, for example, computed tomography techniques.

At least some known coincidence imaging systems use analog electronic circuits to generate a timing signal resulting from the sharp rise in output voltage in the detection device when the detection device detects an event. However, such circuits may have a limited accuracy when the event rate in the detector is very high. Typical trigger circuits often fail to detect events occurring immediately after a preceding event, and when they do detect such events, they detect an event time later than the actual time.

BRIEF SUMMARY OF THE INVENTION

In one aspect, a method for operating a coincidence imaging system is provided. The method includes receiving samples from a detector output and determining an intersection of a first line corresponding to a baseline portion of the detector output samples and a second line corresponding to a pulse rise portion of the detector output samples.

In another aspect, a trigger circuit for a coincidence imaging system is provided. The circuit includes an analog-to-digital converter coupled to a detector output, a set of N accumulators coupled in a circuit parallel to the output of the analog-to-digital converter wherein N is a predetermined value, and a shift register coupled to the output of said plurality of accumulators.

DETAILED DESCRIPTION OF THE INVENTION

Figure 1:
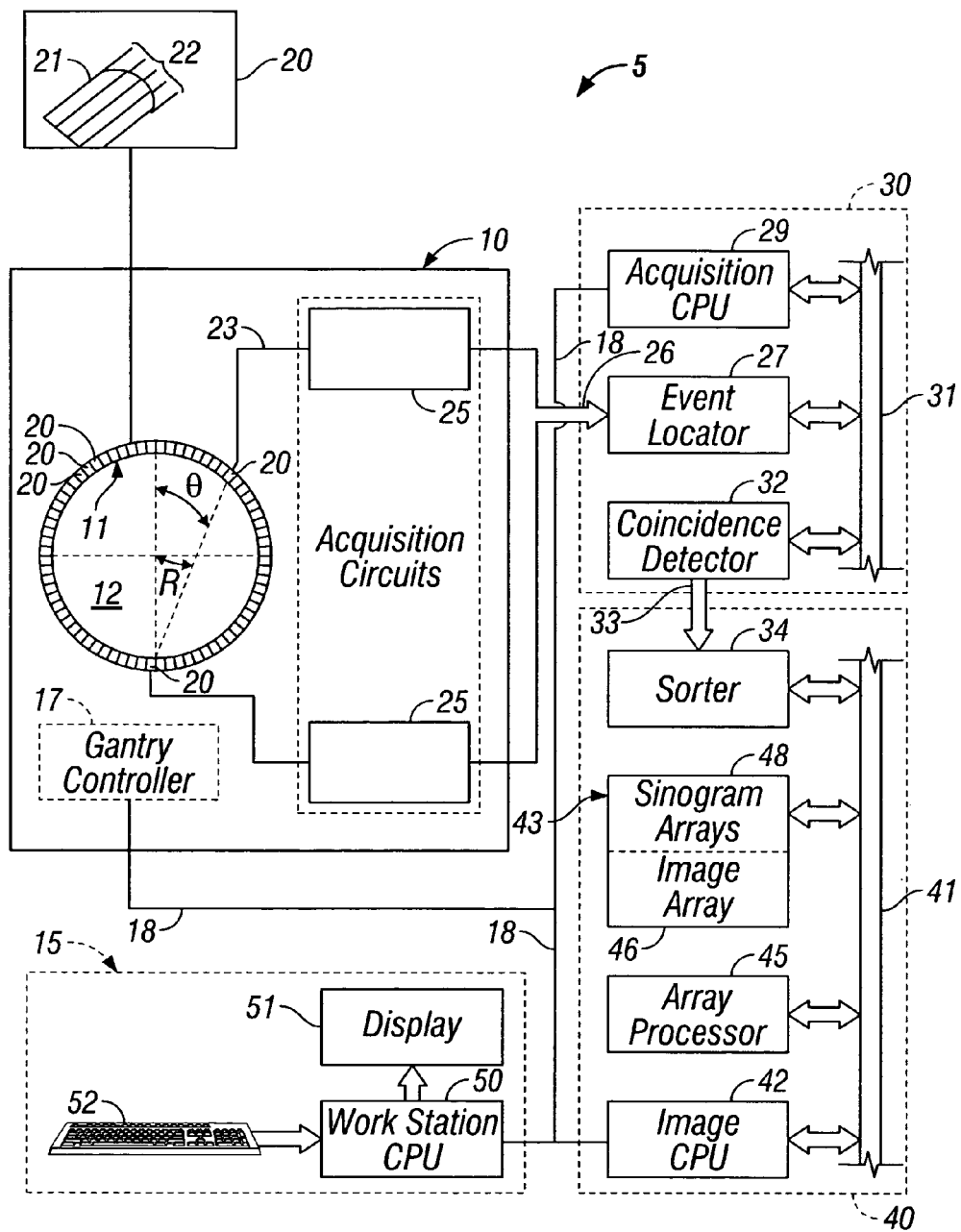
FIG. 1 is a block diagram of an exemplary PET scanner system.

FIG. 1 is a block diagram of an exemplary PET scanner system 5 including a gantry 10 which supports a detector ring assembly 11 about a central opening or bore 12. A patient to be examined is positioned in front of the gantry 10 and is aligned with the central axis of the bore 12. A motorized patient table (not shown) moves the patient into the bore 12 in response to commands received from an operator workstation 15. A gantry controller 17 responds to commands received from operator workstation 15 through a communication link 18, such as, for example, a serial communication link to operate gantry 10.

In this exemplary embodiment, detector ring assembly 11 comprises a plurality of radiation detectors 20. An exploded view of one radiation detector 20 illustrates that each radiation detector 20 includes a set of scintillator crystals 21 (for example, BGO crystals) arranged in a matrix and disposed in front of one or more photomultiplier tubes 22 (PMT) or other light detector. Each PMT 22 produces an analog signal on at least one of a plurality of conductors 23 when a scintillation event occurs. A set of acquisition circuits 25 are mounted within gantry 10 to receive these analog signals and produce digital signals indicating the event coordinates (x,y) and the total energy the scintillation event. The digital signals from each acquisition circuit 25 are sent through a cable 26 to a respective event locator circuit 27 that may be housed in a separate cabinet from gantry 10. Each acquisition circuit 25 also produces a timing signal, which indicates when the scintillation event took place.

The event locator circuits 27 form a portion of a data acquisition processor 30 that periodically processes the signals produced by acquisition circuits 25. Data acquisition processor 30 may have an acquisition CPU 29 that controls communications on communication link 18 and a backplane bus 31. Event locator circuits 27 process and assemble the information regarding each valid event into a set of digital numbers (e.g., event data packet) that include a time marker that indicates when the event took place and the position of scintillation crystal 21 that detected the radiation event. Each event data packet is transmitted to a coincidence detector 32 that also forms a portion of data acquisition processor 30.

Coincidence detector 32 receives the event data packets from event locator circuits 27 and determines if any two of the event data packets are in coincidence. Coincidence is determined by a number of factors. In one embodiment, the time markers in each event data packet must be within 12.5 nanoseconds of each other (or some other value of time window), and second, the locations indicated by the two event data packets must lie on a substantially straight line which passes through the field of view in scanner bore 12 and as described in more detail herein. Events that cannot be paired are discarded, but coincident event pairs satisfying the coincidence requirements are located and recorded as a coincidence data packet that is conveyed through a link 33 (e.g., serial link) to a sorter 34. In another embodiment, the timing signals of two events which are deemed to be in coincidence are used to calculate a time difference. The time difference is the time between the detection of the first event of a coincidence pair and the detection of the second event of the pair.

Figure 2:
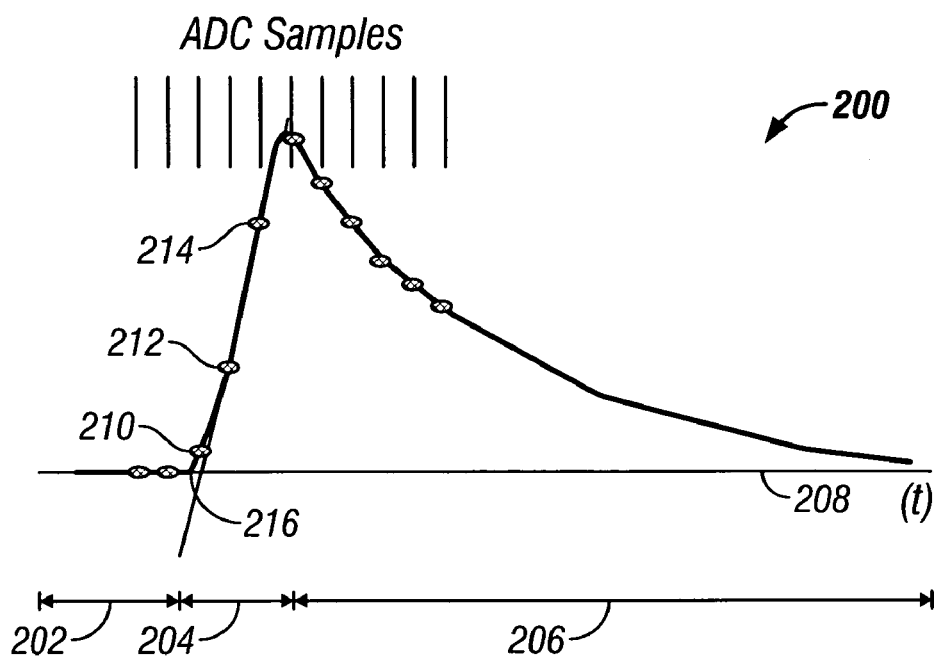
FIG. 2 is a graph of an exemplary event detection pulse output of the PMT shown in FIG. 1.

FIG. 2 is a graph of an exemplary event detection pulse 200 output from PMT 22 (shown in FIG. 1). Pulse 200 includes a baseline portion 202, a pulse rise portion 204, and a decay portion 206. An x-axis 208 represents time and a y-axis 209 represents an amplitude event detection pulse 200. An analog-to-digital converter (not shown) of acquisition circuits 25 digitizes the voltage output from PMT 22 at a rate sufficient to obtain a plurality of samples 210, 212 and 214 during pulse rise portion 204. In an exemplary embodiment, an event start 216 is detected by measuring a voltage difference between successive samples. Because noise may be a significant limitation in gamma ray detection, an event detection algorithm, executing on system 5, detects three successive voltage differences of greater than five percent of the full-scale voltage. In an alternative embodiment, other algorithms may selectably be used.

In this exemplary embodiment, a temporal accuracy of less than one nanosecond may be achieved by determining the time at which a straight line 218 fitted through pulse rise portion 204 intersects a straight line 220 fitted through baseline portion 202.

Figure 3:
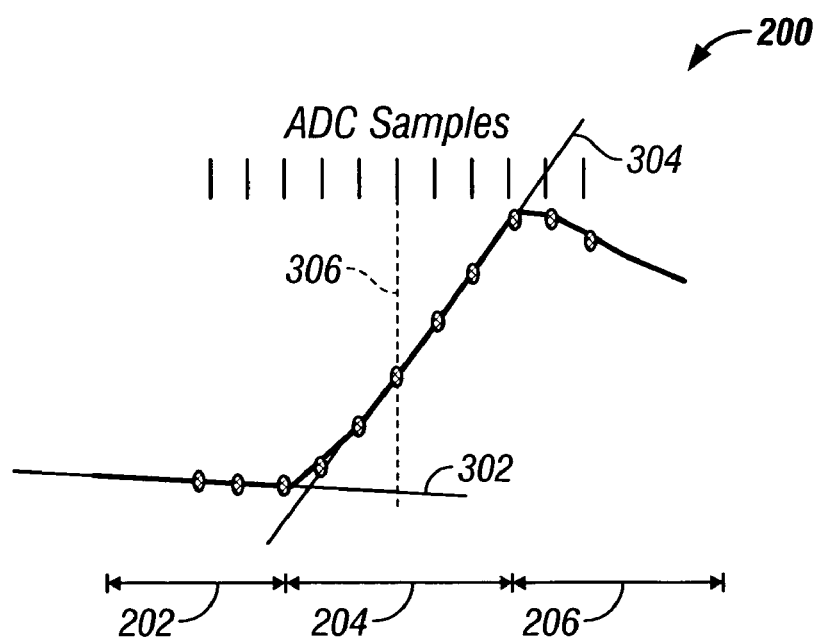
FIG. 3 is an expanded view of the exemplary event detection pulse output shown in FIG. 2.

FIG. 3 is an expanded view of the exemplary event detection pulse 200 (shown in FIG. 2). A difficult event detection situation occurs during relatively high event rates when a new event starts before the previous event is completed. In an exemplary embodiment, an accurate estimate of the actual event time (e.g., the time the gamma ray entered detector 20) is obtained by determining the time where a straight line 302 fitted through baseline portion 202, prior to start of the event, intersects a straight line 304 fitted through pulse rise portion 204.

Pulse rise portion 204 may be fitted to the equation, $$y = m_1 t + b_1,$$

where $m_1$ is the slope and
$b_1$ is the y-intercept.

In the exemplary embodiment, a y-axis 306 (t=0) (shown as a vertical line) arbitrarily may be chosen on pulse rise portion 204, and slope $m_1$ at that point may be determined as the average difference between the measurements immediately preceding and following the chosen y-axis. In an alternative embodiment, a time at which an event detector (not shown), using successive differences, detects the start of an event is selected as y-axis 306. Intercept, $b_1$, with this arbitrary y-axis is the average value of points immediately prior to and immediately following, y-axis 306. In this exemplary embodiment, the baseline slope may be measured similarly, for example using $y = m_2 t + b_2$, where $m_2$ is the slope or the baseline, and $b_2$ is the y-intercept. In an alternative embodiment, the baseline slope may be assumed to be zero. The baseline intercept, $b_2$, is then the average value of measurements made prior to the start of the rise portion 204.

The time of the start of the pulse is then calculated from:

$$t = -(b_1 - b_2)/m_1$$

Result, t, is the time between the start of the event (the point where lines 302 and 304 intersect) and the arbitrary y-axis 306, in units of the sampling interval. This method may be embodied within a software code segment executing on acquisition CPU 29 within system 5 or may be implemented using dedicated firmware or hardware.

Figure 4:
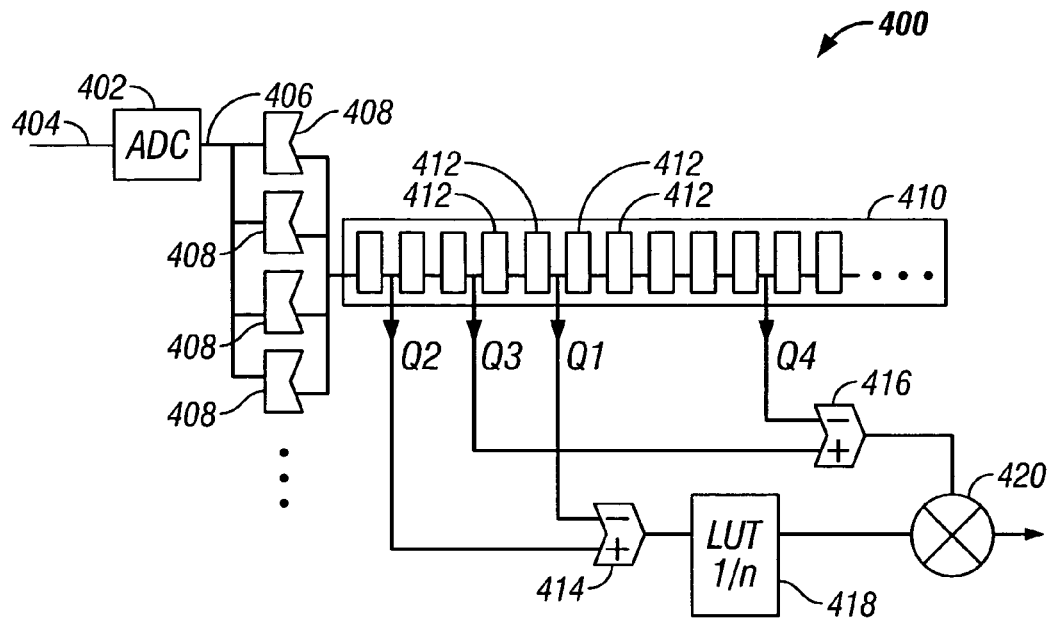
FIG. 4 is a schematic diagram of an exemplary trigger circuit that may be used with the imaging system shown in FIG. 1.

FIG. 4 is a schematic diagram of an exemplary trigger circuit 400 that can be used with imaging system 5 (shown in FIG. 1). Trigger circuit 400 includes an analog-to-digital converter 402 including an input 404 and an output 406. Input 404 is coupled to an output of a photon detector, such as PMT 22. Output 406 is coupled to an input of a plurality of accumulators 408 that are coupled in parallel. An output of each accumulator 408 is coupled to an input of a shift register 410 that includes a plurality of register elements 412. Shift register 410 includes a plurality of outputs, Q1, Q2, Q3, and Q4 that are selected to generate proper delay times for computational accuracy of the pulse samples taken during baseline portion 202 and rise portion 204 of pulse 200. Q1 represents the sum of N values immediately prior to arbitrary y-axis 306. Q2 represents the sum of N values immediately after arbitrary y-axis 306. Q3 represents the sum of N values centered on arbitrary y-axis 306. Q4 represents the sum of N values prior to the start of rise portion 204.

Q1 and Q2 are transmitted to inputs of a computational logic circuit, such as an adder circuit 414 that combines Q1 and Q2 into an output, and in particular, the subtraction of Q1 from Q2 (Q2−Q1). Q3 and Q4 are transmitted to a computational logic circuit, such as an adder circuit 416 that combines Q3 and Q4 into an output Q3−Q4. An output of adder circuit 414 is coupled to an input of a look-up table component 418. An output of look-up table component 418 and an output of the adder 416 are combined by a multiplier 420.

In operation, analog-to-digital converter 402 transmits voltage measurements at a substantially constant rate to the set of N accumulators 408 and shift register 410. Accumulators 408 each sum N successive voltage measurements and output the sums to shift register 410, such that successive elements 412 of shift register 410 contain the following summed voltage measurements:

$$\sum_{i=1}^{N} V_i, \sum_{i=1}^{N} V_{i+1}, \sum_{i=1}^{N} V_{i+2}, \sum_{i=1}^{N} V_{i+3}, \sum_{i=1}^{N} V_{i+4}, \sum_{i=1}^{N} V_{i+5}, \ldots$$

For example, in one embodiment where N=4,
sum1=v1+v2+v3+v4
sum2=v2+v3+v4+v5
sum3=v3+v4+v5+v6
sum4=v4+v5+v6+v7

When an event (i.e., coincidence event) is detected, for example, by a threshold method, four terms, Q1, Q2, Q3, and Q4 are extracted from shift register 410 for processing. A delay in time from coincidence measurement to extraction at the Q4 element is determined by a response of a threshold detector (not shown) and is selected to be sufficient to ensure that in all circumstances, Q4 contains only values prior to rise portion 204. Q4, therefore is the sum of N samples from the ADC prior to the start of the pulse rise, so represents the baseline immediately prior to the start of the rise. Q3 is the sum of N samples centered on some arbitrary time, T, during the rise, so the average of these values should equal the signal value at this arbitrary time. Q2 is the sum of N samples some time after the arbitrary time, T, and Q1 is the sum of N samples preceding the arbitrary time T by the same duration as Q1 lags T. If N were chosen to be 1, then Q3−Q4 would be the signal rise from the baseline to time T, and Q2−Q1 would be the rise from the time Q1 was collected to the time that Q2 was collected. Dividing Q2−Q1 by the time from Q1 to Q2 gives the slope of the rising part of the pulse.

The value of Q3−Q4 represents the value $N*(b_1-b_2)$ and the value of Q2−Q1 represents N values of $(V_{i+k}-V_j)$ where k is the number of sampling intervals between the start of the Q1 and the Q2 sums. If N is selected as a power of 2 (e.g., 2, 4, 6, 8, etc.) then a factor of N can be removed by shifting or by selecting only the most significant bits for subsequent processing. The resulting values $B1=(b_1-b_2)=(Q3-Q4)/N$ and $M1=(Q2-Q1)/N$ are the intercept and slope of the straight line fitting the samples Q1 to Q3, where the y values are relative to the average baseline, $b_2$. The intersection of the rising portion of the pulse with the baseline is the value of (Q3−Q4)/(Q2−Q1) is determined using by look-up table 418 and multiplier 420. This is the time, relative to the arbitrarily defined, T, at which the rising slope intercepts the baseline.

In an exemplary embodiment, using a sodium iodide scintillation detector yields an event rise time of approximately eighty to ninety nanoseconds and a decay time of about eight hundred nanoseconds (with a two hundred thirty nanosecond half-time). Analog-to-digital converter 402, sampling at 200 MHz (i.e., every five nanoseconds) generates approximately sixteen sample values during event pulse rise portion 204. The event detector (not shown) examines differences in every fourth sample, and triggers if three successive such differences exceed a predetermined limit, such as five percent of full scale. Such a limit provides a trigger time about thirty to forty nanoseconds after the start of the event, which becomes the arbitrary y-axis 306 (shown in FIG. 3).

The time calculation uses N=8. With an 8-bit analog-to-digital converter 402, each of the Qn outputs has a range of ten bits, assuming, for example, that the first half of the sampled rise is within the lower half of full scale. The difference Q2−Q1 yields nine bits. The most significant eight bits are used to access a look-up table component 418 with a ten bit inverse value (i.e., one bit whole and nine fractional bits), which in turn is multiplied, using multiplier 420, by the ten bit value, Q3−Q4. The resulting twenty-bit value contains eleven integral bits and nine fractional bits. However, this result is N times the true value of t, and so, if N=8, the result should be interpreted as fourteen integral and six fractional bits. This time value may be entered directly as the event time.

A precise time marker may be generated at a time exactly $T_d$ after the start of the pulse. In the exemplary embodiment, the arbitrary y-axis 306 (shown in FIG. 3) is about 30–40 nanoseconds after the start of the event, accordingly $T_d$ may be selected to equal, eighty nanoseconds (or sixteen sample intervals). Time value, t, calculated as described above, is the time from the start of the event to the arbitrary y-axis 306, thus, the timing pulse should be generated at 16−t intervals after the arbitrary y-axis. (16−t) is calculated and the whole number part loaded into a countdown counter that counts down using the sample clock and generates a timing pulse at zero. This pulse (timed to the preceding clock before the desired time) is then provided to a programmable delay line, which has been loaded with the fractional part of (16−t), such that the pulse is delayed by the fractional part. The integral part of the result can be used to control a countdown timer that is partitioned into three whole number bits, and three or more fractional bits.

Figure 5:
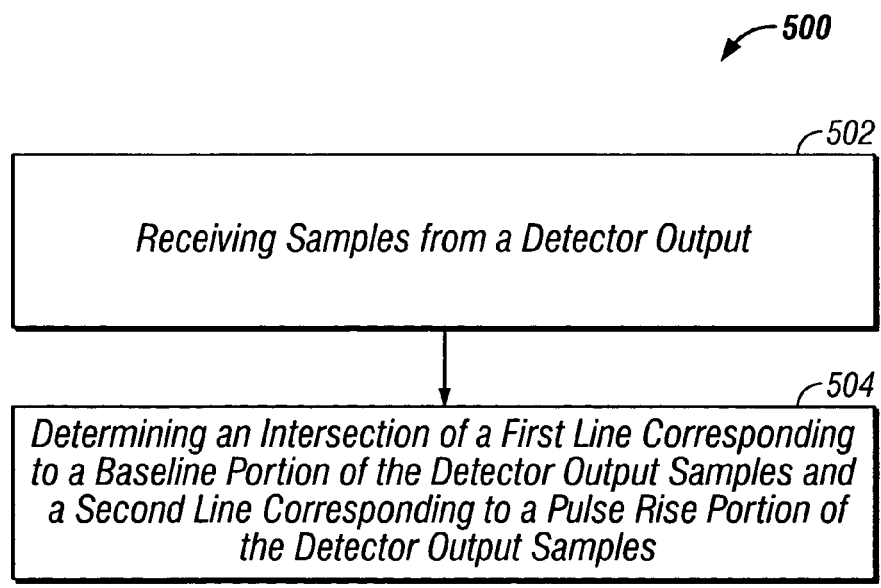
FIG. 5 is a flowchart of an exemplary method that may be used to implement the trigger circuit shown in FIG. 4.

FIG. 5 is a block diagram of an exemplary method 500 that may be used to implement trigger circuit 400 (shown in FIG. 4). Method 500 includes receiving 502 samples from a detector output and determining 504 an intersection of a first line corresponding to a baseline portion 202 of the detector output samples and a second line corresponding to a pulse rise portion 204 of the detector output samples.

Exemplary embodiments of apparatus and methods that facilitate timing coincidence events in a PET scanner are described above in detail. A technical effect of the timing apparatus and methods described herein include at least one of facilitating improving determination of coincidence pairs of positron annihilation events. The timing apparatus and methods include a plurality of logic devices and a processor that allows for controlling a timing trigger and logic outputs.

It will be recognized that although the system in the disclosed embodiments comprises programmed hardware, for example, executed in software by a computer or processor-based control system, it may take other forms, including hardwired hardware configurations, hardware manufactured in integrated circuit form, firmware, among others. It should be understood that the trigger circuit disclosed may be embodied in a digital system with periodically sampled signals, or may be embodied in an analog system with continuous signals, or a combination of digital and analog systems.

The above-described methods and apparatus provide a cost-effective and reliable means for facilitating generating a time signal to perform coincidence imaging. More specifically, the methods and apparatus facilitate improving the accuracy of time signals during periods of relatively high count-rates. As a result, the methods and apparatus described herein facilitate operating coincidence imaging systems in a cost-effective and reliable manner.

Exemplary embodiments of coincidence imaging systems are described above in detail. However, the systems are not limited to the specific embodiments described herein, but rather, components of each system may be utilized independently and separately from other components described herein. Each system component can also be used in combination with other system components.

While the invention has been described in terms of various specific embodiments, those skilled in the art will recognize that the invention can be practiced with modification within the spirit and scope of the claims.

What is claimed is:

1. A method for operating a coincidence imaging system, said method comprising:
   receiving samples from a detector output; and
   determining an intersection of a first line corresponding to a baseline portion of the detector output samples and a second line corresponding to a pulse rise portion of the detector output samples.

2. A method in accordance with claim 1 wherein determining an intersection of a first line and a second line comprises determining an intersection of a first line and a second line wherein the intersection defines an event time.

3. A method in accordance with claim 1 wherein determining an intersection of a first line corresponding to a baseline portion of the detector output samples and a second line corresponding to a pulse rise portion of the detector output samples comprises determining an intersection of a first line corresponding to a baseline portion of the detector output samples wherein the baseline portion is defined by a plurality of detector output samples preceding the pulse rise portion, and a second line corresponding to a pulse rise portion of the detector output samples.

4. A method in accordance with claim 1 further comprising determining the start of an event based upon a voltage difference between successive samples.

5. A method in accordance with claim 1 wherein receiving samples from a detector output comprises sampling a detector output using an analog-to-digital converter.

6. A method in accordance with claim 5 wherein sampling a detector output using an analog-to-digital converter comprises sampling a detector output using an analog-to-digital converter at a predetermined rate that is sufficient to obtain a plurality of samples during the pulse rise portion.

7. A method in accordance with claim 6 wherein N represents a predetermined number of accumulators, and wherein sampling a detector output using an analog-to-digital converter comprises:
   summing N successive voltage measurements; and
   transmitting the sums to a shift register, such that successive elements of the shift register include:

$$\sum_{i=1}^{N} V_i, \sum_{i=1}^{N} V_{i+1}, \sum_{i=1}^{N} V_{i+2}, \sum_{i=1}^{N} V_{i+3}, \sum_{i=1}^{N} V_{i+4}, \sum_{i=1}^{N} V_{i+5}, \ldots$$

8. A method in accordance with claim 7 further comprising:
   detecting a scintillation event; and
   transmitting an output from the shift register to a computational logic circuit.

9. A method in accordance with claim 1 wherein determining an intersection comprises:
   selecting a sampled point on the pulse rise portion as the origin of a y-axis; and
   determining a slope of the second line using the equation, $y=m_2 t+b_2$, where,
   $m_2$ is the slope of the second line; and
   $b_2$ is the intercept of the second line with the y-axis.

10. A method in accordance with claim 1 wherein determining an intersection comprises determining a slope of the first line using the equation, $y=m_1 t+b_1$, where,
   $m_1$ is the slope of the first line; and
   $b_1$ is the intercept of the first line with the y-axis.

11. A method in accordance with claim 1 further comprising determining a time of the intersection from the equation, $t=-(b_1-b_2)/m_1$, where,
   t is the time of the start of the intersection and the y-axis in units of a sampling interval,
   $b_2$ is an average of a predetermined number of baseline samples,
   $b_1$ is an average of a predetermined number of baseline portion samples and a predetermined number of pulse rise portion samples, and
   $m_1$ is the slope of the straight line fitted through the pulse rise portion of the detector output samples.

12. A method in accordance with claim 1 further comprising generating a trigger pulse at a determined time interval after the start of the rise pulse.

13. A method in accordance with claim 12 further comprising time-stamping each trigger pulse.

14. A method for operating a coincidence imaging system, said method comprising:
   sampling a detector output that includes a pulse, that has a baseline portion and a pulse rise portion, using an analog-to-digital converter at a predetermined sample rate, such that the sample rate is sufficient to obtain a plurality of samples during the pulse rise portion;
   determining a slope of a first line fitted through a baseline portion of the detector output samples;
   determining a slope of a second line fitted through a pulse rise portion of the detector output samples;
   determining an intersection of the first line and the second line; and
   determining a time difference between the intersection and a pre-selected sample time of a pulse rise portion sample.

15. A method for determining a coincidence event in a coincidence imaging system, said method comprising:
   defining a first line corresponding to a baseline portion of a plurality of detector output sample values;
   defining a second line corresponding to a pulse rise portion of a plurality of detector output sample values; and
   determining an intersection of the first line and the second line, the intersection represents the time of the coincidence event.

* * * * *